United States Patent
Komatsuzaki et al.

(10) Patent No.: US 6,288,229 B1
(45) Date of Patent: Sep. 11, 2001

(54) RUTHENIUM COMPLEX HAVING DI OR TETRAPYRIDOPHENAZINE LIGAND USEFUL FOR USE AS LUMINESCENT MATERIAL

(75) Inventors: Nobuko Komatsuzaki; Ryuzi Katoh; Yuichiro Himeda; Hideki Sugihara; Hironori Arakawa, all of Tsukuba; Kazuyuki Kasuga, Tsuchiura, all of (JP)

(73) Assignee: Secretary of Agency of Industrial Science and Technology (JP)

(*) Notice: Subject to any disclaimer, the term of this patent is extended or adjusted under 35 U.S.C. 154(b) by 0 days.

(21) Appl. No.: 09/534,964

(22) Filed: Mar. 27, 2000

(30) Foreign Application Priority Data

Aug. 31, 1999 (JP) .................................................. 11-246802

(51) Int. Cl.$^7$ ....................................................... C07F 1/00
(52) U.S. Cl. .......................... 544/225; 544/339; 544/342; 556/137; 252/301.18; 252/700
(58) Field of Search .............................. 252/700, 301.18; 544/225, 339, 342; 556/137

(56) References Cited

PUBLICATIONS

Alford et al., J. Chem. Soc. Perkin Trans. II, No. 5, pp. 705–709 (May 1985).*
Amouyal et al., J. Chem. Soc. Dalton Trans., No. 5, pp. 1841–1845 (Jun. 1990).*
Bolger et al., Inorganic Chemistry, vol. 35, No. 10, pp. 2937–2944 (May 1996).*
Campagna et al., Inorganic Chemistry, vol. 38, No. 4, pp. 692–701 (Feb. 1999).*

\* cited by examiner

*Primary Examiner*—Porfirio Nazario-Gonzalez

(57) ABSTRACT

A ruthenium (II) complex having a dipyridophenazine or tetrapyridophenazine ligand and being represented by the formula (1) or (2) shown in the specification. Upon absorption of light, the complex emits fluorescence for a longer life time in a protic solvent as compared with known analogous compounds.

4 Claims, No Drawings

RUTHENIUM COMPLEX HAVING DI OR TETRAPYRIDOPHENAZINE LIGAND USEFUL FOR USE AS LUMINESCENT MATERIAL

BACKGROUND OF THE INVENTION

This invention relates to a novel Ru(II) complex containing a di or tetrapyridophenazine ligand and having a luminescent property.

Ruthenium (II) complexes having the following formulas:

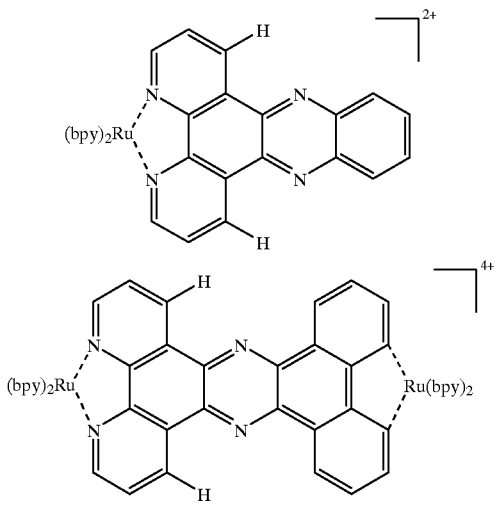

wherein bpy represents bipyridine are known.

These compounds have a luminescent (fluorescent) property. The luminescence of these compounds, however, has a strong solvent dependency. Thus, in the presence of a protic solvent such as water or alcohol, the luminescent characteristic of these compounds disappears. This is perhaps attributed to addition of proton to the nitrogen atom of the pyrazine ring and resulting deactivation of its exciting state. Therefore, applications of the known ruthenium complexes as a sensitizer are considerably restricted.

SUMMARY OF THE INVENTION

It is, therefore, an object of the present invention to provide a novel ruthenium (II) complex which exhibits strong luminescence even in a protic solvent.

In accomplishing the above object, there is provided in accordance with the present invention a ruthenium complex having the following formula (1):

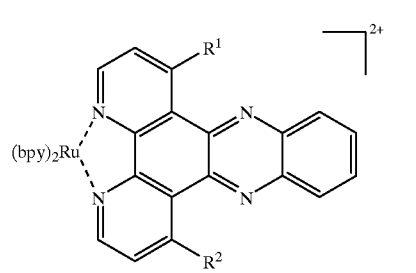

wherein $R^1$ and $R^2$ stand, independent from each other, for an alkyl group having 1–4 carbon atoms and bpy represents bipyridine.

The present invention also provides a ruthenium complex having the following formula (2):

wherein $R^3$ and $R^4$ stand, independent from each other, for an alkyl group having 1–4 carbon atoms and bpy represents bipyridine.

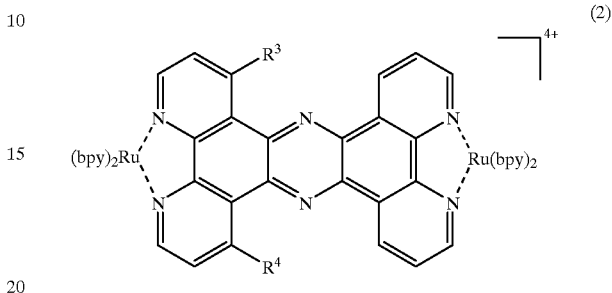

The present invention further provides a sensitizer comprising a solution of the above ruthenium complex dissolved in a protic solvent.

The ruthenium complex according to the present invention has a long luminescent life time even in a protic solvent and is useful as a luminescent material. Especially, the ruthenium complex is utilizable as a sensitizer for use in photoreaction in a protic solvent, for a wet solar cell or for a fluorescent sensor.

Other objects, features and advantages of the present invention will become apparent from the detailed description of the preferred embodiments of the invention to follow.

DETAILED DESCRIPTION OF THE PREFERRED EMBODIMENTS OF THE INVENTION

In the formulas (1) above, $R^1$ and $R^2$ stand, independent from each other, for an alkyl group having 1–4 carbon atoms such as methyl, ethyl, propyl or butyl. The compound of the formula (1) absorbs light of a wavelength in the range of 400–550 nm and can emit fluorescence of a wavelength in the range of 550–750 nm. In the formulas (2) above, $R^3$ nd $R^4$ stand, independent from each other, for an alkyl group having 1–4 carbon atoms such as methyl, ethyl, propyl or butyl. The compound of the formula (2) absorbs light of a wavelength in the range of 400–550 nm and can emit light of a wavelength in the range of 550–800 nm The following examples will further illustrate the present invention.

EXAMPLE 1

Synthesis of Dipyridophenazine/Ru(II) Complex (compound of formula (1) above in which $R^1$ and $R^2$ each represent $CH_3$):

Synthetic scheme is as follows:

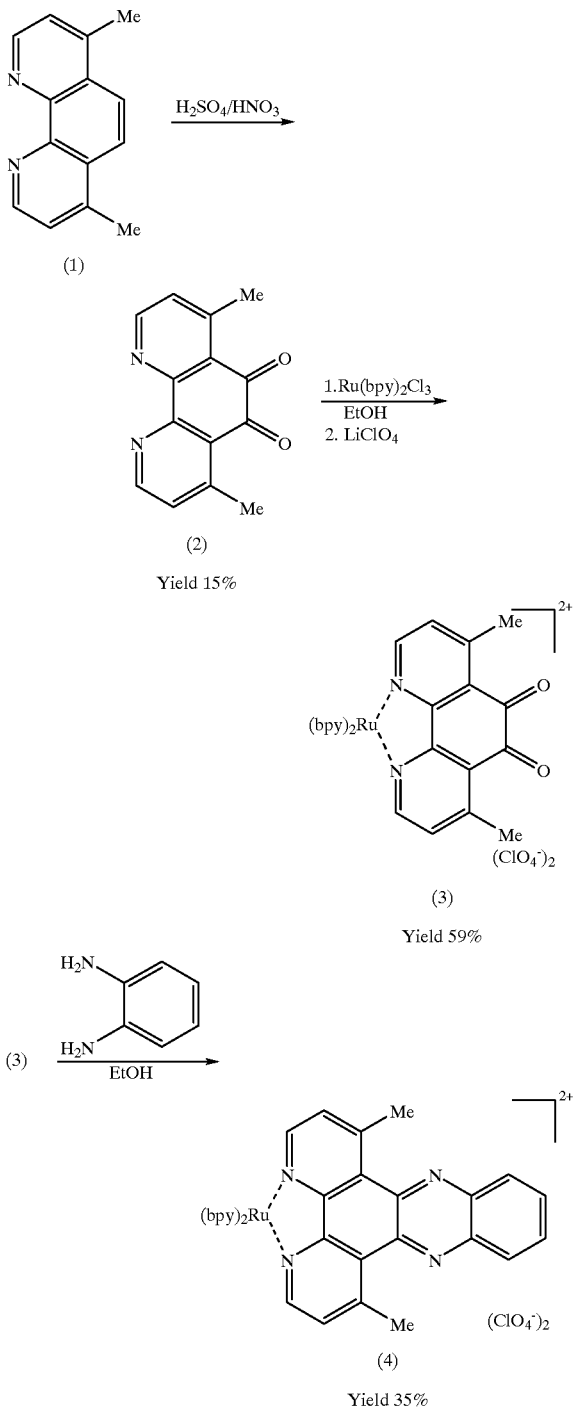

(a) Preparation of 4,7-dimethyl-1,10-phenanthroline-5,6-dione (2):

4,7-Dimethyl-1,10-phenanthroline (1 g, 4.8 mmol) was mixed well with 5.95 g (50 mmol) of potassium bromide and the mixture was placed in a 200 ml flask. The flask was cooled to 0° C., to which 20 ml of concentrated sulfuric acid was slowly added with stirring and, then, 10 ml of concentrated nitric acid was added in a similar manner. The reaction mixture was then heated at 80–85° C. for 2 hours. After being cooled to room temperature, the reaction mixture was poured into 400 ml of water. The aqueous solution was neutralized with sodium hydrogen carbonate, from which a product was extracted twice with 100 ml of methylene chloride. The extract was dried with anhydrous magnesium sulfate. The solvent was then removed by distillation to leave yellow solids. Recrystallization from methanol gave 172 mg of 4,7-dimethyl-1,10-phenanthroline-5,6-dione (2) with a yield of 15%. The structure of the product was confirmed by $^1$HNMR and mass spectroscopy.

$^1$HNMR (CDCl$_3$) δ=2.89 (6H, s, CH$_3$), 7.35 (2H, d, J=4.9 Hz, aromatic), 8.925 (2H, d, J=4.9 Hz, aromatic); FAB Mass M$^+$239 (calculated value: 238)

(b) Preparation of complex (3):

4,7-Dimethyl-1,10-phenanthroline-5,6-dione (60 mg, 0.25 mmol) thus obtained and bis(2,2'-bipyridine)dichloruthenium (II) monohydrate (121 mg, 0.25 mmol) were dissolved in 20–30 ml of ethanol. The solution was heated under reflux for 3 hours under nitrogen atmosphere. This was then cooled to room temperature and concentrated to a volume of about 5 ml. The concentrated solution was mixed with 10 ml of a saturated lithium perchlorate aqueous solution. The dark brown precipitates (complex (3)) thus formed were filtered, washed with a small amount of water and then with ether. This was passed through a column chromatograph (alumina column, elution liquid: acetonitrile:water:potassium nitrate (saturated)=100:10:1) and then recrystallized from ethanol to give 125 mg (yield: 59%) of the complex (3).

Elementary analysis (as RuC$_{34}$H$_{26}$O$_{10}$N$_6$Cl$_2$+H$_2$O):
Calculated: C 47.01, H 3.25, N 9.68
Found: C 46.91, H 3.15, N 9.46

(c) Preparation of complex (4):

Complex (3) (100 mg, 0.12 mmol) thus obtained and 1,2-phenylenediamine (19 mg, 0.18 mmol) were dissolved in 20–30 ml of ethanol. The solution was heated under reflux for 8 hours under nitrogen atmosphere. This was then cooled to room temperature and the solvent was removed to leave solids. The solids were dissolved in a small amount of acetonitrile and the solution was passed through a column chromatograph (alumina column, elution liquid: acetonitrile:water:potassium nitrate (saturated)=100:10:1). Recrystallized from ethanol gave 31 mg (yield: 35%) of the complex (4).

Elementary analysis (as RuC$_{40}$H$_{30}$O$_8$N$_8$Cl$_2$+H$_2$O):
Calculated: C 51.07, H 3.43, N 11.91
Found: C 51.09, H 3.36, N 11.56

EXAMPLE 2

Synthesis of Tetrapyridophenazine/Ru(II) Complex (compound of formula (2) above in which $R^3$ and $R^4$ each represent $CH_3$):

Synthetic scheme is as follows:

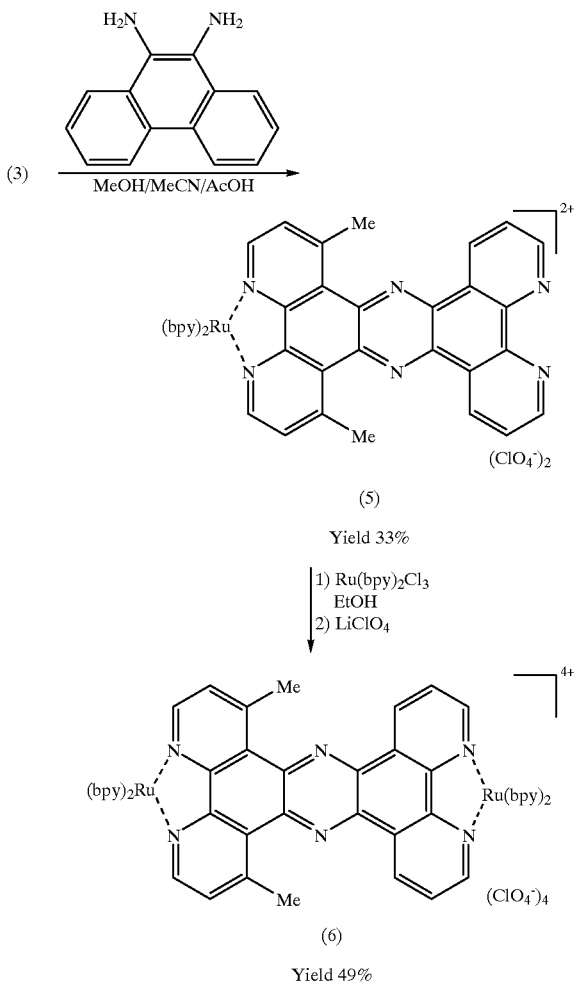

Yield 33%

Yield 49%

(a) Preparation of Complex (5):

Complex (3) (90 mg, 0.11 mmol) obtained in Example 1 and 5,6-diamino-1,10-phenanthroline (24 mg, 0.12 mmol) were dissolved in 20–30 ml of a mixed solvent of methanol:acetonitrile:acetic acid=4:3:1. The solution was heated under reflux for 24 hours under nitrogen atmosphere. This was then cooled to room temperature and the solvent was removed to leave solids. The solids were dissolved in a small amount of acetonitrile and the solution was passed through a column chromatograph (alumina column, elution liquid: acetonitrile:water: potassium nitrate (saturated)=100:10:1). Recrystallized from ethanol gave 37 mg (yield: 33%) of the complex (5).

Elementary analysis (as $RUC_{46}H_{32}O_8N_{10}Cl_2+3H_2O$);
Calculated: C 51.21, H 3.55, N 12.98
Found: C 51.04, H 3.15, N 13.10

(b) Preparation of complex (6):

The complex (5) (56 mg, 0.054 mmol) thus obtained and bis(2,2'-bipyridine)dichloruthenium (II) monohydrate (29 mg, 0.060 mmol) were dissolved in 20–30 ml of ethanol. The solution was heated under reflux for 12 hours under nitrogen atmosphere. This was then cooled to room temperature and concentrated to a volume of about 5 ml. The concentrated solution was mixed with 10 ml of a saturated lithium perchlorate aqueous solution. The red orage precipitates (complex (6)) thus formed were filtered and dissolved in a small amount of acetonitrile. This was passed through a column chromatograph (alumina column, elution liquid: acetonitrile:water:potassium nitrate (saturated)=100:10:1) and then recrystallized from ethanol to give 40 mg (yield: 49%) of the complex (6).

Elementary analysis (as $Ru_2C_{66}H_{48}O_{16}N_{14}Cl_4+H_2O$);
Calculated: C 47.89, H 3.04, N 11.85
Found: C 47.87, H 2.89, N 11.57

EXAMPLE 3

Each of the Ru(II) complexes (5) and (6) obtained in Examples 1 and 2 in acetonitrile and in methanol to give four solutions having a concentration of the complex of $1\times10^{-5}$ M. Each solution was irradiated with light of 450 nm and 2 to measure the fluorescent life time ($\tau$ (ns)). The results are summarized in Tables 1 (in acetonitrile) and 2 (in methanol). Comparative Examples 1 and 2

For the purpose of comparison, similar measurement was carried out using known dipyridophanazine/ruthenium (II) complex (compound of the formula (1) above in which $R^1$ and $R^2$ are each a hydrogen atom; Comparative Example 1) and tetrapyridophanazine/ruthenium (II) complex (compound of the formula (2) above in which $R^3$ and $R^4$ are each a hydrogen atom; Comparative Example 2). The results are also summarized in Tables 1 and 2.

TABLE 1

(in $CH_3CN$)

| Example No. | Absorption λmax (nm) | Emission λmax (nm) | Life time τ (ns) |
|---|---|---|---|
| Example 1 | 456 | 628 | 1160 |
| Comparative Example 1 | 494 | 629 | 740 |
| Example 2 | 443 | 670 | 180 |
| Comparative Example 2 | 443 | 668 | 90 |

TABLE 2

(in $CH_3OH$)

| Example No. | Absorption λmax (nm) | Emission λmax (nm) | Life time τ (ns) |
|---|---|---|---|
| Example 1 | 456 | 621 | 820 |
| Comparative Example 1 | 450 | 624 | 30 |
| Example 2 | 444 | 664 | 100 |
| Comparative Example 2 | 444 | 657 | 30 |

The invention may be embodied in other specific 15 forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A ruthenium complex having the following formula (1):

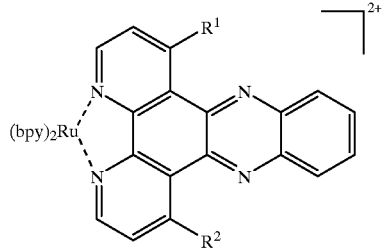

wherein $R^1$ and $R^2$ stand, independent from each other, for an alkyl group having 1–4 carbon atoms and bpy represents bipyridine.

2. A ruthenium complex having the following formula (2):

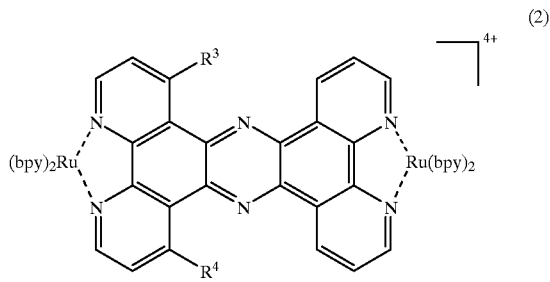

wherein $R^3$ and $R^4$ stand, independent from each other, for an alkyl group having 1–4 carbon atoms and bpy represents bipyridine.

3. A sensitizer comprising a solution of a ruthenium complex according to claim 1 dissolved in a protic solvent.

4. A sensitizer comprising a solution of a ruthenium complex according to claim 2 dissolved in a protic solvent.

* * * * *

UNITED STATES PATENT AND TRADEMARK OFFICE
CERTIFICATE OF CORRECTION

PATENT NO. : 6,288,229 B1  
DATED : September 11, 2001  
INVENTOR(S) : Komatsuzaki et al.

It is certified that error appears in the above-identified patent and that said Letters Patent is hereby corrected as shown below:

Column 5,
Lines 6-15, " 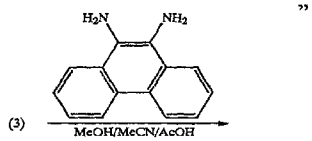 "

should read -- 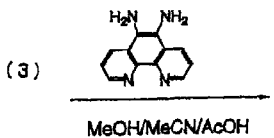 --

Column 6,
Line 62, delete "15"

Signed and Sealed this

Fourth Day of June, 2002

Attest:

Attesting Officer

JAMES E. ROGAN
Director of the United States Patent and Trademark Office